US00PP30317P3

(12) United States Plant Patent
Kleinwee

(10) Patent No.: US PP30,317 P3
(45) Date of Patent: Mar. 26, 2019

(54) ***PETUNIA* PLANT NAMED 'PEHY0029'**

(50) Latin Name: *Petunia hybrida*
Varietal Denomination: PEHY0029

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,584

(22) Filed: Jul. 3, 2017

(65) Prior Publication Data

US 2018/0124981 P1 May 3, 2018

(30) Foreign Application Priority Data

Oct. 31, 2016 (QZ) ..... PBR 2016/2638

(51) Int. Cl.
*A01H 5/02* (2018.01)

(52) U.S. Cl.
USPC ..... Plt./356.21
CPC ..... *A01H 5/02* (2013.01)

(58) Field of Classification Search
USPC ..... Plt./356.21, 356.1
CPC ... A01H 5/02; A01H 5/00; A01H 6/82; A01H 6/1424; A01H 6/824
See application file for complete search history.

(56) References Cited

U.S. PATENT DOCUMENTS

| | | | | |
|---|---|---|---|---|
| PP16,468 | P3 * | 4/2006 | Miyazaki | A01H 5/02 Plt./356.21 |
| PP18,498 | P3 * | 2/2008 | Oud | A01H 5/02 Plt./356.21 |
| PP23,644 | P2 * | 5/2013 | Hanes | A01H 5/02 Plt./356.1 |
| PP28,030 | P3 * | 5/2017 | van Kleinwee | Plt./356.22 |

* cited by examiner

*Primary Examiner* — June Hwu
(74) *Attorney, Agent, or Firm* — Dale Skalla

(57) ABSTRACT

A new *Petunia plant* named 'PEHY0029' particularly distinguished by medium sized, rose flowers, early flowering and a semi-trailing to mounding plant habit.

1 Drawing Sheet

Latin name of the genus and species of the plant claimed: *Petunia hybrida.*

Varietal denomination: 'PEHY0029'.

BACKGROUND OF THE NEW PLANT

The present invention comprises a new *Petunia*, botanically known as *Petunia hybrida*, and hereinafter referred to by the variety name 'PEHY0029'.

'PEHY0029' is a product of a planned breeding program. The new cultivar has medium sized, rose flowers, early flowering and a semi-trailing to mounding plant habit.

'PEHY0029' originated from a hybridization made in October 2011 in a controlled breeding environment in Enkhuizen, The Netherlands. The female parent was the commercial variety *petunia* 'SANGUNA Purple Improved' (Not protected in US) with purple flower color and a comparable plant habit with some more vigor.

The male parent of 'PEHY0029' was the unpatented line 'H9189-2', a plant with comparable plant habit and a salmon colored flower and late flowering.

The resulting seeds were sown in January 2012. 'PEHY0029' was selected as one flowering plant within the progeny of the stated cross in May 2012 in a controlled environment in Enkhuizen, The Netherlands.

The first act of asexual reproduction of 'PEHY0029' was accomplished when vegetative stem tip cuttings were propagated from the initial selection in June 2012 in a controlled environment in Angers, France.

BRIEF SUMMARY OF INVENTION

Horticultural examination of plants grown from cuttings of the plant initiated in June 2012 and continuing thereafter, has demonstrated that the combination of characteristics as herein disclosed for 'PEHY0029' are firmly fixed and are retained through successive generations of asexual reproduction.

'PEHY0029' has not been observed under all possible environmental conditions. The phenotype may vary significantly with variations in environment such as temperature, light intensity, and day length.

A Plant Breeder's Right for this cultivar was applied for in the European Union on Oct. 31, 2016, No. 2016/2638. 'PEHY0029' has not been made publicly available prior to the effective filing date of this application, notwithstanding any disclosure that may have been made less than one year prior to the effective filing date of this application by the inventor or another who obtained 'PEHY0029' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0029' with colors being as true as possible with an illustration of this type.

Figure 1:
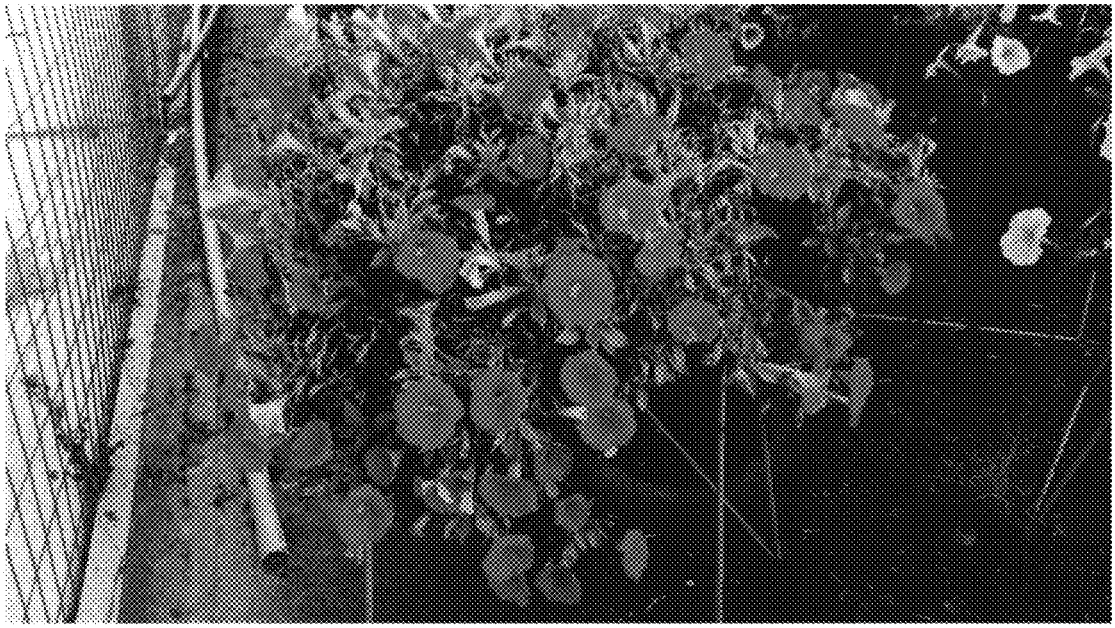
Figure 2:
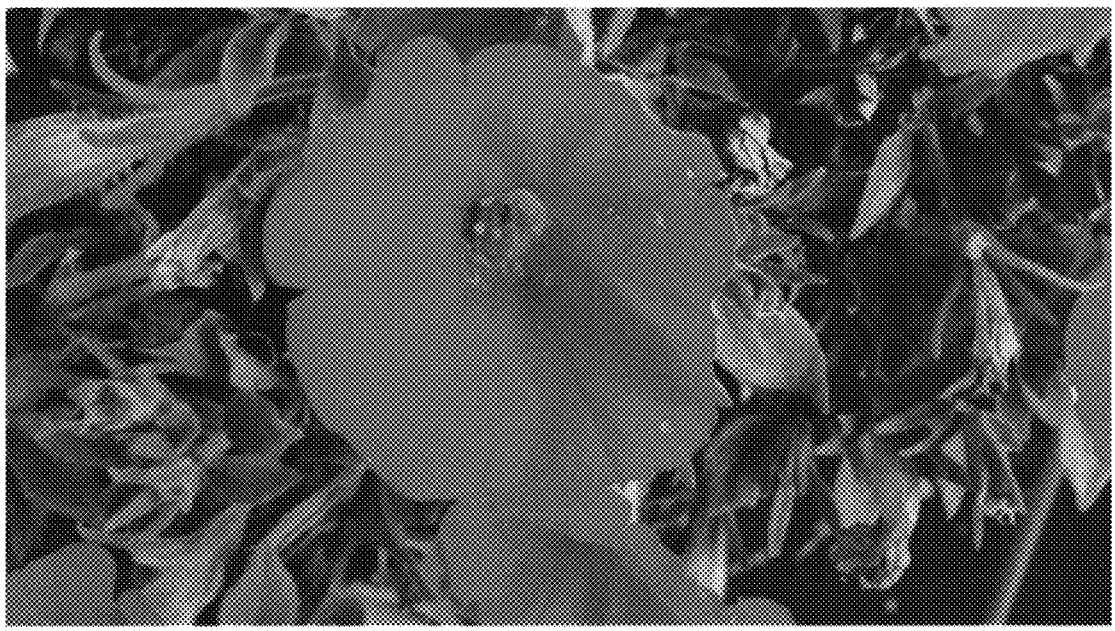

The photographic drawing shows in FIG. 1. a flowering plant of the new variety and in FIG. 2. a close-up of the flowers.

DETAILED BOTANICAL DESCRIPTION

The aforementioned photographs were taken in September 2016 from plants growing outside in Andijk, The Netherlands. These plants were approximately 22 weeks of age.

The plant descriptions and measurements were taken in October 2016 in Enkhuizen, Netherlands on 23 week old plants that were growing in 25 cm pots.

Color references are made to The Royal Horticultural Society Colour Chart (R.H.S.) 2001.

TABLE 1

DIFFERENCES BETWEEN THE NEW VARIETY 'PEHY0029' AND A SIMILAR VARIETY

| | 'PEHY0029' | 'Petrosena' (U.S. Plant Pat. No. 18,498) |
|---|---|---|
| Plant habit: | Semi-trailing to mounding, very good branching | Semi-upright, less branching |
| Earliness: | Early flowering | Late flowering |
| Flower color: | Less intense color | Intense color N57A |

Plant:

*Form, growth and habit.*—Semi-trailing to mounding plant habit.
*Plant height.*—17 cm.
*Plant height (inflorescence included).*—19 cm.
*Plant diameter (width).*—60 cm.

Roots:

*Number of days to initiate and produce roots.*—16 days at about 22 degrees C.
*Type.*—Fine, fibrous, free branching.
*Color.*—RHS N155B.

Foliage:

*Arrangement.*—Alternate, simple.
*Immature leaf, color upper surface.*—RHS 144A.
*Immature leaf, color lower surface.*—RHS 144B.
*Mature leaf, color upper surface.*—Darker than RHS 144A.
*Mature leaf, color lower surface.*—RHS 144A.
*Length.*—4 cm.
*Width.*—1.6 cm.
*Shape.*—Ovate.
*Base shape.*—Attenuate.
*Apex shape.*—Acute.
*Margin.*—Entire.
*Texture, upper surface.*—Moderate covered with short hair.
*Lower surface.*—Densely covered with very short hairs.
*Color of veins, upper surface.*—RHS 144B.
*Color of veins, lower surface.*—RHS 144B.
*Petiole color.*—RHS 144B.
*Length.*—0.4-0.7 cm.
*Diameter.*—0.2 cm.
*Petiole texture.*—Short glandular hair.

Stem:

*Quantity of main branches per plant.*—5-6.
*Color of stem.*—RHS 146C.
*Length of stem.*—35-40 cm.
*Diameter.*—0.4 cm.
*Length of internodes.*—1-3 cm.
*Texture.*—Dense, mostly glandular hairs of various lengths.
*Color of pedicel.*—RHS 146C.
*Length of pedicel.*—1.0-3 cm.
*Diameter of pedicel.*—0.2 cm.
*Texture of pedicel.*—Densely covered with short hairs.

Inflorescence:

*Type.*—Flowers solitary in upper leaf axis.
*Floret type.*—Funnel-shaped; 5 lobed petals; fused at the base.
*Blooming habit.*—Early flowering in greenhouse, flowering throughout the summer months.
*Quantity of inflorescences per plant.*—Approximately 60.
*Lastingness of individual blooms on the plant.*—About 7 days.
*Fragrance.*—A little scent.

Bud (just when opening):

*Color.*—RHS N81C with green veins RHS 144C.
*Length.*—3.5 cm.
*Width.*—0.6 cm.
*Shape.*—Oblong.

Immature inflorescence:

*Flower horizontal diameter.*—3.5 cm.
*Color petals, upper surface.*—RHS N57A.
*Color petals, lower surface.*—RHS 75C with green veins RHS 144B.

Mature flower:

*Flower horizontal diameter.*—5.5 cm.
*Flower height (vertical).*—3.5 cm.
*Color upper surface.*—RHS N57A.
*Color lower surface.*—RHS 75C with green veins RHS 144B.
*All petals.*—
*Apex shape.*—Truncate to retuse.
*Margin.*—Entire.
*Waviness of margin.*—Weak.
*Petal lobation.*—Little.
*Petal texture, upper surface.*—Papillose, glabrous.
*Petal texture, lower surface.*—Glandular hairs, more dense on veins and tube.
*Corolla tube color outside.*—RHS 144C.
*Corolla tube color inside.*—RHS N82D, more green, RHS 144C towards base.
*Corolla tube length.*—2.5 cm.
*Corolla tube texture, outside.*—Dense glandular hairs of different size.
*Corolla tube texture, inside.*—Glabrous.

Calyx:

*Color of sepal, upper surface.*—RHS 144A.
*Color of sepal, lower surface.*—RHS 144A.
*Length.*—2.7 cm.
*Width.*—0.3-0.4 cm.
*Shape.*—Ensiform.
*Apex shape.*—Acute to obtuse.
*Base.*—Fused.
*Margins.*—Entire.
*Texture, upper surface.*—Densely covered with short glandular hairs.

*Lower surface*.—Densily covered with short glandular hairs.

Reproductive organs:

*Pistil*.—1.

*Length*.—2.2 cm.

*Style color*.—RHS 150C.

*Style length*.—2 cm.

*Stigma color*.—RHS 150B.

*Stamens*.—

*Quantity per flower*.—5.

*Color of filaments*.—RHS 150D, sometimes very little anthocyanin at top.

*Length filaments*.—2 cm.

*Anther color*.—RHS 155A.

*Anther length*.—0.15 cm.

*Anther shape*.—Elliptical.

*Color of pollen*.—RHS 155A.

*Pollen amount*.—Abundant.

*Fertility/seed set*.—Has not been observed on this hybrid.

*Disease/pest resistance*.—Has not been observed on this hybrid.

What is claimed is:

1. A new and distinct variety of *Petunia* plant named 'PEHY0029' substantially as illustrated and described herein.

* * * * *